United States Patent [19]

Raghunathan

[11] 4,221,778
[45] Sep. 9, 1980

[54] PROLONGED RELEASE PHARMACEUTICAL PREPARATIONS

[75] Inventor: Yegnaswami Raghunathan, Fairport, N.Y.

[73] Assignee: Pennwalt Corporation, Philadelphia, Pa.

[21] Appl. No.: 1,644

[22] Filed: Jan. 8, 1979

Related U.S. Application Data

[63] Continuation of Ser. No. 800,105, May 24, 1977, abandoned, which is a continuation-in-part of Ser. No. 745,325, Nov. 26, 1976, abandoned.

[51] Int. Cl.$^2$ .................. A61K 47/00; A61K 9/22; A61K 9/30; A61K 31/74
[52] U.S. Cl. .................. 424/31; 424/32; 424/33; 424/38; 424/79
[58] Field of Search .................. 424/31, 32, 33, 38, 424/79

[56] References Cited

U.S. PATENT DOCUMENTS

| | | | |
|---|---|---|---|
| 3,138,525 | 6/1964 | Koff | 424/79 |
| 3,143,465 | 8/1964 | Keating | 424/79 |
| 3,487,046 | 12/1969 | Negrevergne | 424/38 |
| 3,499,960 | 3/1970 | Macek | 424/79 X |
| 3,594,470 | 7/1971 | Borodkin | 424/79 X |
| 3,629,394 | 12/1971 | Gaunt | 424/79 X |

FOREIGN PATENT DOCUMENTS

| | | | |
|---|---|---|---|
| 729827 | 9/1969 | Belgium | 424/79 |
| 2246037 | 4/1974 | Fed. Rep. of Germany | 424/79 |
| 1003241 | 9/1965 | United Kingdom | 424/78 |

OTHER PUBLICATIONS

Borodkin, J. Pharm. Sci., vol. 60, Oct. 1971, pp. 1523–1527.

*Primary Examiner*—Anna P. Fagelson

[57] ABSTRACT

Prolonged release pharmaceutical preparations containing ion exchange resin drug complexes at least a substantial portion of which have been treated with a solvating agent and provided with a diffusion barrier coating.

8 Claims, No Drawings

PROLONGED RELEASE PHARMACEUTICAL PREPARATIONS

This is a continuation of application Ser. No. 800,105, filed May 24, 1977, which in turn is a continuation-in-part of application Ser. No. 745,325 filed Nov. 26, 1976, both abandoned.

This is a continuation-in-part of application Ser. No. 745,325, filed Nov. 26, 1976.

The present invention relates to prolonged continuous release pharmaceutical preparations containing an ion exchange resin having a pharmacologically active drug adsorbed thereon to provide a drug resin complex wherein at least a portion of the complex is treated with a solvating agent and provided with a diffusion barrier coating.

PRIOR ART

The basic patent on the use of (uncoated) ion exchange resin drug complexes to delay release of a drug in the gastrointestinal tract is U.S. Pat. No. 2,990,332. However, such uncoated complexes provide only a relatively short delay of drug release in comparison with the preparations of this invention and provide no means for selectively modifying the release profile.

Various coated resins and resin drug complexes have been reported (e.g., in U.S. Pat. No. 3,138,525; 3,499,960 and 3,594,470; Belgian Pat. No. 729,827; German Pat. No. 2,246,037; and Brodkins et al, Journal of Pharmaceutical Science, Vol. 60, pages 1523–1527, 1971), but none are believed to employ the preparations of the subject invention or to provide the prolonged continuous release obtainable with the present preparations.

BRIEF SUMMARY OF THE INVENTION

The present invention is concerned with pharmaceutical preparations comprised of ion exchange resins having a pharmacologically active drug adsorbed thereon to form a drug-resin complex wherein at least a substantial portion of the complex particles have been treated with a solvating agent and provided with a water-permeable diffusion barrier coating whereby a prolonged continuous release of the drug is obtainable under conditions encountered in the gastrointestinal tract.

DETAILED DESCRIPTION

It has now been found that a selective, prolonged continuous release of pharmacologically active drugs, under conditions such as those encountered in the gastrointestinal tract, can be achieved by the application of diffusion barrier coatings to ion exchange resin drug complex particles which have been treated with solvating agents.

In general all acidic and basic drugs, especially those having short biological half-lives in the order of up to about 8 hours, are potential candidates for inclusion in the subject preparations. Examples are phenylpropanolamine (PPA), dextromethorphan, ephedrin, pseudoephedrine, paraamino salicyclic acid, acetyl salicylic acid, phentermine (phenyl-tertiary-butyl-amine), and acetaminophen. PPA, a sympathomimetic amine drug with a biological half life of 3.9 hours in man and a pKa of 9.4 was chosen as a model drug for use in the bulk of the illustrative examples. The loading of the drug on the resin particles can be from about 1–90 percent by weight, although 15–50 percent is the normal practical range.

Similarly, a wide range of cationic (for the basic drugs) or anionic (for the acidic drugs) exchange resins can be used to form the drug resin complex, particle sizes normally ranging from about 75 to 1000 um. The illustrative examples employ Amberlite IR-120, a cationic exchange resin consisting of 20–30 mesh (590–840 um) spherical particles as a model large particle resin and Amberlite XE-69, which is 100–200 mesh fractured resin particles of Amberlite IR-120, as a model small particle resin. The parent resin of IR-120 and XE-69 is described by the manufacturer as gel-type divinylbenzene sulfonic acid cation exchange resin which swells in water with a pH range of 0–14. Other suitable ion exchange resin candidates include synthetic ion exchange resins with different polymeric matrices (e.g., methacrylic, acrylic, phenol formaldehyde), ion exchange agents with cellulosic or dextran polymer matrices, and inorganic ion exchange matrices. The resins should not have inherent pharmacological or toxic properties.

Adsorption of the drug onto the ion exchange resin particles to form the drug resin complex is a well-known technique as shown in U.S. Pat. No. 2,990,332 and demonstrated in the examples hereinbelow. In general, the drug is mixed with an aqueous suspension of the resin and the complex is then dried. Adsorption of drug onto the resin is detected by a change in the pH of the reaction medium.

As shown by the illustrative examples below, such resin drug complexes rapidly release the drug in the gastrointestinal tract, e.g., an Amberlite IR-120 phenylpropanolamine complex with a 35 percent drug loading released 61 percent of the drug in 60 minutes in a 0.1 normal hydrochloric acid dissolution medium (Example 1). Initial attempts to retard this rapid release of drug by the use of diffusion barrier coatings were relatively ineffective as shown by Examples 1 and 2 below since the coating tended to peel rapidly and the coated particles swelled and tended to fracture when contacted by water or biological fluids. It has now been discovered that the tendency of ion exchange resin drug complex particles to swell and fracture in biological fluids can be overcome by the use of solvating agents such as polyethylene glycol. The solvating agent can be added as an ingredient in the resin drug complexation step or preferably, the particles can be treated with the solvating agent after complexing. This treatment has not only been found to help the particles retain their geometry, but has enabled the effective application of diffusion barrier coatings to such particles. A model solvating agent chosen for use in the illustrative examples is polyethylene glycol 4000, a normally solid hydrophilic agent. Other effective solvating (impregnating) agent candidates include, for example, propylene glycol, mannitol, lactose and methylcellulose. Up to about 30 parts by weight (normally 10–25 parts) of the solvating agent to 100 parts by weight of the resin has been found to be effective. As shown in Example 3, such pretreatment of drug resin complex particles has enabled the effective application thereto of diffusion barrier coatings, resulting in the ability to effectively prolong the release of drugs from drug resin complexes.

The water-permeable, diffusion barrier coating materials can in general be any of the conventional synthetic or natural film-forming materials with diffusion barrier properties and with no inherent pharmacological or toxic properties. Ethylcellulose, a water insoluble film forming agent was used as the model diffusion barrier membrane material in the illustrative examples. A plasticizer, Durkex 500 vegetable oil, was used to improve the film forming characteristics of ethylcellulose. The amount of coating used depends on the degree of drug release prolongation desired.

Conventional coating solvents (such as ethanol or a methylene chloride/acetone mixture) and procedures can be employed to coat the particles. In the illustrative examples, coatings were carried out by using an air suspension spray coating technique using a Wurster coating apparatus. Techniques of fluid bed spray coating are taught, for example, in U.S. Pat. Nos. 3,089,824; 3,117,027; and 3,253,944. The coating is normally applied to the drug resin complex, but alternatively can be applied to the resin before complexing with the drug.

Dissolution data in Examples 4–16 below demonstrates that the prolonged, continuous release of drugs from drug resin complex particles is now obtainable by use of solvating agents and diffusion barrier coatings, and that the dissolution profiles of such coated complexes are relatively unaffected by the various conditions encountered in the gastrointestinal tract. It is also demonstrated that variation in the amount of coating and/or the use of coated/uncoated complex mixtures can now be employed to selectively modify the dissolution profile as desired. Biological availability studies reported in Example 17 and 18 confirm the dissolution profile results and demonstrate practical administration of the subject preparations in syrup and capsule form. In addition to oral administration, the preparations of the subject invention are also suitable for topical, rectal, vaginal or nasal administration in dosages varying over a wide range, for example from about 0.1 to about 1000 mg, depending on the nature of the drug and its intended usage. The compositions can take the form of tablets, powders, capsules, liquid suspensions or other conventional dosage forms.

ILLUSTRATIVE EXAMPLES

The following dissolution test apparatus and procedures were used in the examples to simulate conditions encountered in the gastrointestinal tract: 500 milliliters (ml.) of the selected dissolution medium (0.1 N HCl—pH of 1.2; or 0.1 N HCl plus NaCl to show effect of chloride ions; or 0.1 M phosphate buffer—pH of 7.5) was placed in a one liter cylindrical jacketed beaker. The dissolution medium was maintained at 37°±0.5° C., by circulating warm water through the jacket from a water bath. A three-bladed polyethylene stirrer was positioned eccentrically in the dissolution beaker and rotated at 60 revolutions per minute. A polymer foam cylindrical sparger extending into a regular plastic tube was positioned diametrically opposite the stirrer. The dissolution medium filtered into this tube from where it was pumped by a finger pump through a polyethylene tube into a five centimeter (cm.) cell path flow through cell and returned to the beaker. A double beam ultraviolet spectrophotometer (Beckman Model Dk-2A) was used to monitor the changes in the absorption at the selected ultraviolet wavelength (257 nm for phenylpropanolamine) as a function of time on a moving chart as the drug was released from a drug resin complex sample (equivalent to 70 milligrams of drug) agitated in the dissolution medium. The drug released was then expressed as a percentage of the total drug present in the resin complex particles.

Microscopic examinations of particles of resin were carried out using a Bausch and Lomb low power binocular microscope (objective X3 and eyepiece X10).

Diffusion barrier coatings were carried out using an air suspension coating technique employing a Wurster coating apparatus (such as made by Aeromatic U.S., Inc., Glatt Air Techniques, Inc. and Dairy Equipment Corp.).

Examples 1 and 2 illustrate the effect of omitting the diffusion barrier coating (such as ethyl cellulose) and/or the use of pretreatment agents (such as polyethylene glycol) from drug resin complexes based on phenylpropanolamine (PPA).

EXAMPLE 1 a. Preparation of Amberlite IR-120 Phenylpropanolamine Complex (35% theoretical load):

| | |
|---|---|
| Amberlite IR-120 Resin-Hydrogen Cycle (10% moisture) | 3611 gm |
| Phenylpropanolamine Base | 1750 gm |

Procedure:

The resin was placed in about 10 liters of deionized water. The phenylpropanolamine base was added with low agitation. The mixing was continued for 5 hours. Initial pH of the slurry was 2.5 pH of the suspension during addition of phenylpropanolamine was 8.0. The final pH of the suspension was 1.7. The resin complex was collected on a buchner funnel and tray dried at 45° C. in an air oven. The following dissolution was obtained on the uncoated resin drug complex.

| TIME, MINUTES | % PHENYLPROPANOLAMINE RELEASED IN 0.1 N HCl |
|---|---|
| 15 | 32 |
| 30 | 48 |
| 60 | 61 |

Microscopic examination showed some fractured resin particles.

b. Coating of (a) above:

| | |
|---|---|
| IR-120 - PPA resin complex from (a) above | 100 gm. |
| Ethylcellulose | 3 gm. |
| Ethanol 95% | 60 ml. |

Procedure:

Ethylcellulose was dissolved in ethanol. The resin complex was placed in a fluid bed coating apparatus and fluidized. The ethylcellulose solution was slowly applied to the fluidized resin particles at room temperature. After all of the solution was applied, the particles were further dried for a few minutes.

Microscopic examination of the particles revealed that the coating was uniformly applied. There were some broken particles present too:

The following dissolution data was obtained:

| TIME, MINUTES | % PHENYLPROPANOLAMINE RELEASED IN 0.1N HCl |
|---|---|
| 15 | 15 |
| 30 | 26 |
| 60 | 42 |

The data shows that some retardation of dissolution of the drug resin complex is achieved by coating the particles, though not to a significant extent.

EXAMPLE 2

Example 1 was substantially repeated using 550 gm. of Amberlite XE-69 Phenylpropanolamine Resin Complex (about 25% drug load) as the core material; 75 gm. of ethylcellulose (50 cps) and 30 gm. of of Durkex 500 refined vegetable oil as the coating agents; and 140 ml. of acetone and 1260 ml. of methylene chloride as the solvents.

The coating agents were dissolved in the mixed solvents with stirring and quantitatively applied on the core in a 6 inch fluid bed apparatus at the rate of approximately 8 ml./minute (total time—205 minutes). The inlet air temperature range was 140°–160° F. The outlet air temperature range was 88°–95° F.

The average particle size of the coated particles was 96 um. Microscopic examination of the particles showed the coating of the particles to be peeling.

The following dissolution data was obtained:

| TIME, MINUTES | % PHENYLPROPANOLAMINE RELEASED IN 0.1N HCl | |
|---|---|---|
| | COATED | UNCOATED |
| 15 | 57 | 82 |
| 30 | 76 | 88 |
| 60 | 87 | 92 |
| 90 | 91 | 95 |

The data again shows that coating alone only leads to slight retardation of dissolution.

Repeats of Examples 1 and 2 produced equivalent results, the coating being observed to peel readily in all the tests. Also, when the coated particles were brought in contact with water, they swelled considerably and tended to fracture. These problems were overcome when the ion exchange resin drug complex particles were treated with polyethylene glycol 4000 as described in the following example:

EXAMPLE 3 a. Preparation of Amberlite IR-120 Phenylpropanolamine Complex:

| | |
|---|---|
| Amberlite IR-120 resin (hydrogen cycle - 10% moisture) | 2167 gm. |
| Phenylpropanolamine | 1050 gm. |

The resin was placed in 7 liters of deionized water in a suitable beaker and mixed for 20 minutes to hydrate. Initial pH was noted to be 2.5. The phenylpropanolamine base was gradually added with mixing. It was then set aside. The final pH was 1.7. The resin complex was collected on a buchner funnel and tray dried in an air oven at 45° C.

b. Preparation of Polyethylene Glycol Treated complex:

| | |
|---|---|
| Resin Complex from (a) | 900 gm. |
| Polyethylene glycol 4000 | 100 gm. |

The resin complex was placed in a suitable jacketed planetary mixer. The polyethylene glycol 4000 was added and gently mixed with application of gentle heat. When the polyethylene glycol 4000 completely melted (56° C.) the heat was turned off. The mixing was continued until the temperature returned to room temperature. The resin particles were gently passed through #20 mesh screen to remove any agglomerates. Very few agglomerates were noted to be present. The following dissolution data was obtained:

| TIME, MINUTES | % PHENYLPROPANOLAMINE RELEASED IN 0.1N HCl |
|---|---|
| 15 | 26 |
| 30 | 39 |
| 60 | 47 | c. Preparation of Coated Complex from b.

100 gm. of the polyethylene glycol treated resin complex from (b) above was placed in a fluid bed spray coating apparatus and fluidized and coated with a solution of ethylcellulose (10 cps) in ethanol 95% (6 gm. in 300 ml.). The coated particles were dried for a few additional minutes after all the solution had been applied. The coated beads were examined microscopically and were observed to possess fairly good coating.

The following dissolution data was obtained:

| TIME, MINUTES | % PHENYLPROPANOLAMINE RELEASED IN 0.1N HCl |
|---|---|
| 15 | 9 |
| 30 | 18 |
| 60 | 28 |

This data indicates that good retardation of the dissolution rate of drug resin complex particles is obtained by application of a diffusion barrier coating when the particles are treated with agents such as polyethylene glycol.

The following examples (4–16) illustrate application of the above discovery to prepare formulations representative of the subject invention:

EXAMPLE 4 a. Preparation of Amberlite IR-120 Phenylpropanolamine Resin Complex:

| | |
|---|---|
| Amberlite IR-120 resin (wet hydrogen cycle) | 600 gm. (288 gm. dry) |
| Phenylpropanolamine base | 155 gm. |
| Polyethylene glycol 4000 | 72 gm. |
| Deionized water | 1000 ml. |

72 gm. of polyethylene glycol 4000 was dissolved in 1000 ml. of deionized water. The resin was added to this solution with gentle mixing. Phenylpropanolamine was added gradually with gentle mixing. The mixing was continued until the pH dropped to 1.9. It was then set aside for 24 hours. The solution was drained off from the resin complex.

b. Preparation of Coating Solution

| | |
|---|---|
| Ethylcellulose (50 cps.) | 5 gm. |
| Durkex 500 - refined vegetable oil | 2 gm. |
| Ethanol 95% | 200 ml. |

Durkex 500 was added to ethanol 95% with stirring. The solution was warmed to 45° C. Ethylcellulose 50 cps was dissolved in it with mixing. The solution was maintained at 45° C. during the coating.

c. Coating of Amberlite IR-120-Phenylpropanolamine Resin Complex 178.6 gm. of the resin complex from (a) (100 gm. dry resin) was placed in the fluid bed coating apparatus. The resin complex was fluidized and partially dried (time 25 minutes) at room temperature. The coating solution (b) was then sprayed on the resin complex gradually until all of the solution had been applied (time 90 minutes). The air supply was at room temperature. The coated particles were dried for 5 more minutes at the end of the application of the coating solution. The dry coated particles were gently screened through #20 mesh screen.

Microscopic examination showed the particles to be smooth and uniformly coated. No fractured particles were noted to be present.

The particles had a moisture content of 4%. Phenylpropanolamine content was 31.6%.

The following dissolution was obtained. Good retardation of the dissolution rate is evident by comparison of the uncoated control (data in second column) to the dissolution data for the coated particles (third, fourth and fifth columns) regardless of the pH of ionic concentration of the media.

cps) was dissolved in it with mixing. The solution was maintained at 45° C. during the coating.

C. Coating of Amberlite IR-120—Phenylpropanolamine Resin Complex 178.6 gm. of the resin complex from (a) (100 gm. dry resin) was placed in the fluid bed coating apparatus. The resin complex was fluidized and partially dried at room temperature. The coating solution (b) was then sprayed on the resin complex gradually until all of the solution had been applied. The air supply was at room temperature. The coated particles were dried for 5 more minutes at the end of the application of the coating solution. The dry coated particles were gently screened through #20 mesh screen.

Microscopic examination of the particles showed the particles to be smooth and uniformly coated. No fractured particles were noted to be present. The final moisture was 3.6%. Phenylpropanolamine content was 30.7%.

The following dissolution data was obtained in 0.1 N HCl and 0.1 M phosphate buffer pH 7.5.

| | % PHENYLPROPANOLAMINE RELEASED | | | |
|---|---|---|---|---|
| | UNCOATED | COATED IR-120 PPA | | |
| TIME (HOURS) | IR-120 PPA CONTROL 0.1N HCl | 0.1N HCl | 0.1N HCl + NaCl | 0.1M PHOSPHATE BUFFER pH 7.5 |
| 0.25 | | 2.5 | 2.5 | 2.2 |
| 0.50 | 46 | 6.3 | 6.3 | 6.3 |
| 1.0 | 64 | 15 | 13 | 14 |
| 1.5 | 76 | 21 | 19 | 20 |
| 2.0 | | | 27 | 27 |
| 3.0 | | | 37 | 35 |
| 4.0 | | | 46 | 44 |
| 5.0 | | | 53 | 50 |
| 6.0 | | | 60 | 59 |
| 7.0 | | | 64 | 70 |
| 8.0 | | | 69 | 73 |

EXAMPLE 5

The above example was repeated to indicate reproducibility.

a. Preparation of Amberlite IR-120 Phenylpropanolamine Resin Complex

| | |
|---|---|
| Amberlite IR-120 resin "wet" (hydrogen cycle) | 600 gm. (288 gm. dry) |
| Phenylpropanolamine base | 155 gm. |
| Polyethylene glycol | 72 gm. |
| Deionized water | 1000 ml. |

72 gm. of polyethylene glycol 4000 was dissolved in 1000 ml. of deionized water. The resin was added to this solution with gentle mixing. 155 gm. of phenylpropanolamine was added gradually with gentle mixing. The mixing was continued until the pH dropped to 2.0. It was then set aside for 24 hours. The solution was drained off from the resin complex.

b. Preparation of Coating Solution

| | |
|---|---|
| Ethylcellulose (50 cps.) | 5 gm. |
| Durkex 500 - refined vegetable oil | 2 gm. |
| Ethanol 95% | 200 ml. |

Durkex 500 was added to ethanol 95% with stirring. The solution was warmed to 45° C. Ethylcellulose (50

| TIME, HOURS | % PHENYLPROPANOLAMINE RELEASED IN | |
|---|---|---|
| | 0.1N HCl | 0.1M PHOSPHATE BUFFER pH 7.5 |
| 0.25 | 3.0 | 4.2 |
| 0.50 | 6.3 | 8.9 |
| 1.0 | 13 | 17 |
| 1.5 | 18 | 24 |
| 2.0 | 25 | 30 |
| 3.0 | 34 | 40 |
| 4.0 | 42 | 49 |
| 5.0 | 48 | 52 |
| 6.0 | 55 | 62 |
| 7.0 | 59 | 68 |

As can be seen, the dissolution data are similar to the data obtained in Example 4.

Both these examples show that the dissolution rate of drug from a resin drug complex such as Amberlite IR-120 phenylpropanolamine can be significantly modified by the application of a diffusion barrier coating such as that of ethylcellulose and the use of a treating agent such as polyethylene glycol.

The examples also show that the rate of drug release from ethylcellulose coated particles are not significantly affected by pH or high ionic concentration.

Dissolutions have also been carried out in distilled water on these coated resin complexes as well as uncoated resin complexes. No significant release of drug have been noted from either.

EXAMPLES 6–8

Examples 4–5 were again repeated in 500 gm. (Example 6) and 1000 gm. (Example 7) quantities. The dissolution data from these examples as well as from Examples 4–5 are summarized in Table 1 below.

Example 8, the data for which is also summarized in Table 1 illustrates how the present discovery can be utilized in practice to achieve desired dissolution profiles for drugs intermediate between the rates for the uncoated and coated drug resin complexes by using mixtures thereof. The Example 8 dissolution profile is achieved by preparing a mixture of 30 percent of the uncoated IR-120 PPA resin complex and 70 percent of the coated resin complex of Example 7.

TABLE 1

| Example | % PPA Released in 0.1N HCl (Hours) | | | | | | | | |
|---|---|---|---|---|---|---|---|---|---|
| | 0.5 | 1 | 1.5 | 2 | 3 | 4 | 5 | 6 | 7 | 8 |
| Uncoated Control | 46 | 64 | 76 | — | — | — | — | — | — | — |
| 4 | — | 13 | 19 | 27 | 37 | 46 | 53 | 60 | 64 | 69 |
| 5 | — | 13 | — | 25 | 34 | 42 | 48 | 55 | 59 | — |
| 6 | — | 12 | — | 22 | 30 | 41 | 49 | 56 | 60 | — |
| 7 | — | 14 | — | 25 | 36 | 45 | — | — | — | — |
| 8 | 21 | 33 | 40 | 47 | 55 | 60 | 64 | 69 | 74 | — |

Another means of adjusting the dissolution profile made possible by the present discovery is to vary the amount of coating. The following example illustrates the result of using one-half the amount of coating materials employed in Examples 4–5.

EXAMPLE 9 a. Preparation of Amberlite IR-120 Phenylpropanolamine Resin Complex:

| | |
|---|---|
| Amberlite IR-120 resin "wet" (hydrogen cycle) | 1800 gm. (864 gm. dry) |
| Phenylpropanolamine base | 465 gm. |
| Polyethylene glycol 4000 | 216 gm. |
| Deionized water | 3000 ml. |

216 gm. of polyethylene glycol 4000 was dissolved in 3000 ml. of deioized water. The resin was added to this solution with gentle mixing. 465 gm. of phenylpropanolamine was added gradually with gentle mixing. The mixing was continued until the pH dropped to 2.0. It was then set aside. The solution was drained off from the resin complex.

b. Preparation of coating solution:

| | |
|---|---|
| Ethylcellulose 50 cps. | 2.5 gm. |
| Durkex 500 - refined vegetable oil | 1 gm. |
| Ethanol 95% | 100 ml. |

Durkex 500 was added to ethanol 95% with stirring. The solution was warmed to 45° C. Ethylcellulose (50 cps.) was dissolved in it with mixing. The solution was maintained at 45° C. during the coating.

c. Coating of Amberlite IR-120—Phenylpropanolamine Resin Complex:

181.8 gm. of the resin complex from (a) (100 gm. dry basis) was placed in the fluid bed coating apparatus. The resin complex was fluidized and partially dried at room temperature. The coating solution (b) was then sprayed on the resin complex gradually until all of the solution had been applied. The air supply was at room temperature. The coated particles were dried for 5 more minutes at the end of the application of the coating solution. The dry coated particles were screened through #20 mesh screen.

Microscopic examination of the particles showed the particles to be smooth and uniformly coated. No fractured particles were noted to be present. The final moisture was 6.5%. Phenylpropanolamine content was 30%. The following dissolution was obtained:

| TIME, HOURS | % PHENYLPROPANOLAMINE RELEASED IN 0.1N HCl |
|---|---|
| 0.25 | 12 |
| 0.50 | 23 |
| 1.0 | 37 |
| 1.5 | 48 |
| 2.0 | 54 |
| 3.0 | 66 |
| 4.0 | 73 |
| 5.0 | 78 |
| 6.0 | 81 |
| 7.0 | 85 |

The above data shows that the retardation of dissolution is a function of the amount of coating applied.

The following examples (10–15) illustrate the subject invention using Amberlite XE-69 in place of the Amberlite IR-120 used in Examples 4–9.

EXAMPLE 10 a. Preparation of Polyethylene Glycol Treated Amberlite XE-69 Phenylpropanolamine Resin Complex

| | |
|---|---|
| Amberlite XE-69 - Phenylpropanolamine Resin Complex (24% drug load) | 3000 gm. |
| Polyethylene glycol 4000 | 750 gm. |
| Deionized water | 3000 ml. |

The polyethylene glycol was dissolved in the deionized water and the Amberlite XE-69 phenylpropanolamine complex added to it and mixed. The mixture was set aside for an hour and then placed in an air oven and allowed to dry at 58° C. until the moisture was about 10%. It was then screened through a 100 mesh screen prior to coating. The average particle size was observed to be 82 μm.

b. Preparation of coating solution:

| | |
|---|---|
| Ethylcellulose 50 cps | 74.9 gm. |
| Durkex 500 (refined vegetable oil) | 29.7 gm. |
| Acetone | 140 ml. |
| Methylene Chloride - sufficient quantity to make | 1400 ml. |

Ethylcellulose and the vegetable oil were dissolved in the solvents.

c. Coating Procedure

The above resin drug complex core material was fluidized in a suitable fluid bed apparatus that had been provided with a filter bed to retain fine particle materials. The coating solution was applied continuously to the particles at 8.5 ml./minute. (Application time: 182 minutes). The solvent was allowed to evaporate off continuously as it was applied. The temperature of the inlet air ranged between 140°–153° F. The temperature of the outlet air ranged between 87°–97° F. A screen analysis was obtained on the coated particles. The average particle size was observed to be 115 μm.

Microscopic examination showed the particles to be uniformly coated. When treated with water, the particles did not swell as much as the uncoated particles.

The following dissolution was obtained: Retardation of dissolution is evident in the coated product.

| | % PHENYLPROPANOLAMINE RELEASED | | |
|---|---|---|---|
| | | COATED PARTICLES AMBERLITE XE-69 PPA | |
| TIME HOURS | UNCOATED CONTROL PARTICLES AMBERLITE XE-69 PPA (0.1N HCl) | 0.1N HCl | 0.1M PHOSPHATE BUFFER pH 7.5 |
| 0.25 | 82 | 24 | 24 |
| 0.50 | 88 | 34 | 35 |
| 1.0 | 92 | 45 | 50 |
| 1.5 | 95 | 52 | 58 |
| 2.0 | 97 | 57 | 63 |
| 3.0 | | 64 | 71 |
| 4.0 | | 68 | |
| 5.0 | | 71 | |
| 6.0 | | 74 | |
| 7.0 | | 77 | |

EXAMPLES 11–15

Table 2 below summarizes the dissolution data obtained from four additional runs (Examples 11-14) of coated XE-69 PPA particles prepared as in Example 10 in comparison to the uncoated control.

As with Example 8, the Example 15 data again illustrates adjustment of the dissolution profile by using a 30/70 mixture of uncoated and coated particles from Example 10.

TABLE 2

| | % PPA Released in 0.1N HCl (Hours) | | | | | | | | |
|---|---|---|---|---|---|---|---|---|---|
| Example | 0.25 | 0.5 | 1 | 1.5 | 2 | 3 | 4 | 5 | 6 | 7 |
| Uncoated Control | 82 | 88 | 92 | 95 | 97 | — | — | — | — | — |
| 11 | 20 | 29 | 42 | 50 | 55 | — | — | — | — | — |
| 12 | 16 | 27 | 38 | 46 | 52 | — | — | — | — | — |
| 13 | 11 | 21 | 34 | 42 | 48 | — | — | — | — | — |
| 14 | — | 24 | 35 | 42 | 47 | — | — | — | — | — |
| 15 | — | 45 | 52 | 57 | 61 | 66 | 69 | 71 | 73 | 76 |

EXAMPLE 16

This example shows the use of high load of drug in the fine particle resin complex. The retardation of the drug release after coating from these small sized, high drug content particles is as significent as in the examples with lower drug concentration previously described (Examples 10-15). The Amberlite IRF-66 resin used herein is the same as Amberlite XE-69 except that it has a higher heavy metal limit and thus is given a different grade number. This particular batch of IRF-66 met the XE-69 heavy metal limit and thus is in fact the same product.

a. Preparation of Amberlite IRF-66 Phenylpropanolamine Resin Complex high load.

| | |
|---|---|
| Amberlite IRF-66H hydrogen cycle fine particle resin | 1740 gm. |
| Phenylpropanolamine base | 1260 gm. |
| Deionized Water | 6 liters |

The Amberlite IRF-66H resin was suspended in about 6 liters of deionized water with stirring. The phenylpropanolamine base was gradually added. The stirring was continued till the reaction was complete as noted by stabilization of pH. The resin complex was then collected on a buchner funnel, washed with deionized water and dried. The dried product was screened through a #60 mesh screen and assayed. Phenylpropanolamine content was found to be 44.96%. The average particle size was observed to be 82 μm.

b. Preparation of Coated Amberlite IRF-66 Phenylpropanolamine Resin Complex.

| | |
|---|---|
| Amberlite IRF-66 Phenylpropanolamine Resin Complex (44.9% drug load) | 440 gm. |
| Polyethylene Glycol 4000 | 110 gm. |
| Purified Water | 176 ml. |

The Amberlite IRF-66 phenylpropanolamine resin complex was placed in a suitable mixer. The polyethylene glycol 4000 was dissolved in the specified quantity of deionized water and added gradually to the resin complex in the mixer. The mass was well mixed and dried in a fluid bed drier. The dried material was then screened through #60 mesh screen. The screened particles were then coated in a fluid bed coating apparatus with the following coating solution:

| | |
|---|---|
| Ethylcellulose 50 cps | 75 gm. |
| Durkex 500 (refined vegetable oil) | 30 gm. |
| Acetone | 140 ml. |
| Methylene Chloride | 1400 ml. |

The coating conditions were as follows: inlet temperature 86°–102° F., outlet temperature 74°–88° F., coating time 160 minutes.

Rate of application of coating solution: 8.75 ml/minute. The coated material was screened through a #40 screen to discard any unusually large particles. The average particle size of the screened particles was observed to be 155 μm. Microscopic examination showed the particles to be well coated. The following dissolutions were obtained on the uncoated and coated Amberlite IRF-66 phenylpropanolamine resin complex. The retardation of dissolution in the coated product is evident.

As described in the other examples coated/uncoated mixtures of these high load drug resin complexes can be made to match any desired dissolution profile.

| | % PHENYLPROPANOLAMINE RELEASED IN 0.1N HCl | |
|---|---|---|
| Time Hours | Uncoated Complex Particles | Coated Complex Particles |
| 0.25 | 67 | 14 |

-continued

| Time Hours | % PHENYLPROPANOLAMINE RELEASED IN 0.1N HCl | |
|---|---|---|
| | Uncoated Complex Particles | Coated Complex Particles |
| 0.50 | 71 | 22 |
| 1.0 | 73 | 28 |
| 1.5 | 74 | 32 |
| 2.0 | — | 35 |
| 3.0 | — | 39 |
| 4.0 | — | 43 |

EXAMPLE 17

Bioavailability studies were conducted on dogs using the coated and uncoated resin drug complex particles as a preliminary to testing the same in man:

a. Amberlite IR-120 PPA Resin Complex—A crossover study using four dogs compared the urine recovery and blood levels of PPA obtained after administration of the IR-120 PPA resin complex coated or uncoated (from Example 4) at 10 mg. of PPA/kg. of body weight. The results showed significant differences in the blood drug concentration profile for the two formulations in the animals. The apparent elimination half-life for PPA in the coated sample was observed to be 13.3 hours versus 8.6 hours with the uncoated sample.

b. Amberlite XE-69 PPA Resin Complex—The crossover study was repeated using the XE-69 PPA resin complex coated and uncoated (from Example 10) with similar results. The apparent elimination half-life for PPA in the coated sample was observed to be 9.5 hours as against the uncoated sample value of 4.4 hours.

EXAMPLE 18

Based on the data from the dog bioavailability studies, prolonged release dosage forms were formulated for human study to contain mixtures of coated and uncoated particles such that a fraction of the mixture was readily available as the priming dosage (the uncoated particles) and the remaining fraction as the prolonging dosage (the coated particles). Initially, a desirable dissolution profile for PPA was selected and all drug resin complex mixtures were prepared to meet this ideal dissolution profile.

Ten healthy volunteers particpated in this crossover bioavailability study. The following five formulations were evaluated as per the dosages given for each formuation:

A. 10 ml. every 12 hours of a resin drug complex suspension of (1) The 70/30 coated/uncoated mixture of the XE-69 PPA resin complex of Example 15 in an amount equivalent to 37.5 mg. of PPA hydrochloride per 5 ml.; (2) Amberlite XE-69 chlorpheniramine resin complex uncoated in an amount equivalent to 4.0 mg. of chlorpheniramine maleate per 5 ml; and (3) flavored syrup base sufficient to make up the remaining 5 ml.

B. 5 ml. every 6 hours of a formulation equivalent to formulation A except that the syrup base contains the drugs as their salts in solution rather than the drug resin complex particles.

C. 2 capsules every 12 hours of a resin drug complex capsule containing the same ingredients as in formulation A except that corn starch is substituted for the flavored syrup base.

D. 2 capsules every 12 hours of a resin drug complex capsule as in formulation C except that the resin in the resin complex is Amberlite IR-120 rather than XE-69, the IR-120 PPA resin complex mixture being that described in Example 8.

E. 1 capsule every 6 hours of a formulation as described in formulation B except that corn starch is substituted for the syrup base.

Heparinized blood samples were collected from each volunteer at 0, 0.5, 1, 2, 3, 4, 5, 6, 8, 10, 12, and 24 hours. A 6 ½ and 7 hour collection was taken from those subjects receiving regimens B and E. Also, two 24 hour urine collections were obtained from each subject. The plasma was separated from each blood sample and analyzed for drug content.

The data show that:

1. The maximum plasma levels derived from the Amberlite XE-69 resin complex coated formulations A and C are equivalent to those obtained from the soluble salts formuations B and E. Those from the Amberlite IR-120 preparation (D) are less than those produced by (E).

2. The 12 hour plasma levels obtained from all resin formulations are equivalent to or greater than the minimum level, at 6 hours reached by the salt formulations.

3. The absorption rate of Phenylpropanolamine appears to be slightly greater when it has been administered as the salt formulation. Correspondingly, the peak levels are delayed for the drug derived from the resin complex formulations.

4. From area under plotted curve measurements, the bioavailability of drug derived from Amberlite XE-69 formulations is equivalent to (or greater than) that obtained with the salt formulations. The data are confirmed from urine recovery results. While urine recovery appears to indicate that the IR-120 formulation is bioequivalent to the salt formulation, area under the curve measurement suggest that it may not be as great. The results from the bioavailability study indicate that Amberlite XE-69 Phenylpropanolamine formulations prepared as described in this invention possess the desirable properties of a prolonged release delivery system, that is (a) quick release properties as demonstrated by the rapid onset of plasma levels; and (b) delays of peak and prolongation of plasma levels that indicate prolonged release.

5. Comparison of the drug recovered in the urine demonstrates bioequivalency of these modified resin formulations and the salt formulations. Further, these modified resin formulations resulted in maintenance of blood levels over a 12 hour interval after administration of a single dose. The blood levels at peak were not greater than the accepted safe blood levels of the PPA salt. Also, at 12 hours, the values are equal to or greater than the minimum levels observed 6 hours after administration of the generally accepted efficacious salt dose regimen.

6. The data confirms the dissolution profile results indicating that effective prolonged release of drugs are achieved by employing the formulations of the subject invention.

The following examples illustrate the use of other drugs within the scope of the subject invention:

EXAMPLE 19

Dextromethorphan: Dextromethorphan (pKa 8.25) has no analgesic or addictive properties. It acts centrally to elevate the threshold for coughing. Its effectiveness in patients with pathological cough has been demonstrated to be about the equal of codeine. Unlike codeine it rarely produces drowsiness. Its toxicity is quite low. The average adult dose is 10–20 mg., three to four times daily or every 6 to 8 hous a day. Dextromethorphan is thus a candidate drug for prolonged release dosage form.

a. Preparation of Amberlite XE-69 Dextromethorphan Resin Complex:

Amberlite XE-69-Dextromethorphan resin complex was prepared with a drug load of 23.5%. The following dissolution profile was obtained for dextromethorphan uncoated resin complex.

| TIME, MINUTES | % DEXTROMETHORPHAN RELEASED IN 0.1N HCl |
|---|---|
| 15 | 21 |
| 30 | 43 |
| 60 | 60 |
| 90 | 71 |
| 120 | 73 |
| 180 | 76 |
| 240 | 79 |
| 300 | 80 |

The uncoated resin complex appears to be slightly faster in dissolution profile than the desirable ideal, viz—about 50% released in about two hours. Therefore, it might be beneficial to have a mixture of coated-/uncoated resin complex to provide the "ideal" dissolution.

b. Preparation of Polyethylene Glycol treated Amberlite XE-69 Dextromethorphan resin Complex:

| | |
|---|---|
| Amberlite XE-69 Dextromethorphan resin complex | 1840 gm. |
| Polyethylene glycol 4000 | 460 gm. |
| Deionized water | 736 ml. |

The resin complex was weighed into a planetary mixer bowl. The polyethylene glycol was dissolved in the water and the final solution was added to the resin complex slowly with mixing. The material was dried in an oven at 50° C. and then screened through a 60 mesh screen.

c. Preparation of coated Amberlite XE-69 Dextromethorphan Resin Complex (low level coating)

| | |
|---|---|
| Core: | |
| Amberlite XE-69 Dextromethorphan Resin complex polyethylene glycol treated (from b above) | 550 g |
| Coating: | |
| Ethylcellulose 50 cps | 37.5 g |
| Durkex 500 - refined vegetable oil | 15.0 g |
| Solvent: | |
| Acetone | 70 ml |
| Methylene Chloride | 700 ml |

The coating agents were dissolved in the solvents as described in the previous examples and the solution applied on the core material in a fluid bed apparatus. The inlet air temperature ranged from 120°–130° F. and the outlet air temperature ranged from 77°–92° F.

The following dissolution data was observed:

| TIME, MINUTES | % DEXTROMETHORPHAN RELEASED IN 0.1N HCl |
|---|---|
| 15 | 7 |
| 30 | 14 |
| 60 | 22 |
| 90 | 29 |
| 120 | 34 |

It can be readily seen from the above data that dissolution has been well retarded.

d. Preparation of coated Amberlite XE-69 Dextromethorphan Resin Complex (high level coating)

| | |
|---|---|
| Core: | |
| Coated XE-69 Dextromethorphan Resin complex from c above | 301.5 g |
| Coating: | |
| Ethylcellulose 50 cps. | 9.37 g |
| Durkex 500 - refined vegetable oil | 3.75 g |
| Solvent: | |
| Acetone | 17.5 ml |
| Methylene Chloride | 175 ml |

The coating of the core from (c) above was continued further in this experiment with the coating solution as given above. This formula provided twice the level of coating provided under (c).

The following dissolution was obtained:

| TIME, MINUTES | % DEXTROMETHORPHAN RELEASED IN 0.1N HCl |
|---|---|
| 15 | 2 |
| 30 | 5 |
| 60 | 11 |
| 90 | 15 |
| 120 | 19 |

It is evident from the above data that increasing the level of coating decreases the dissolution of dextromethorphan from the resin complex particles. Thus coated/uncoated mixtures of dextromethorphan resin complex can be made to match any desirable dissolution profile as exemplified under phenylpropanolamine examples.

EXAMPLE 20

Pseudoephedrine: Pseudoephedrine is a sympathomimetic agent. It is used in the dose range of 25–60 mg. It has been used as a nasal and bronchial decongestant in doses of 60 mg twice or three times daily. It has a pKa of 9.7 and a biological half life of 5–7 hours in man. Pseudoephedrine is thus a candidate for prolonged release dosage form.

a. Preparation of Amberlite XE-69 Pseudoephedrine Resin Complex:

| | |
|---|---|
| d - Pseudoephedrine Hydrochloride | 317.4 gm |
| Amberlite XE-69 Sodium (anhydrous) | 776.0 gm |
| Deionized water | 3240 ml |

The pseudoephedrine hydrochloride was dissolved in water and the Amberlite XE-69 added and the two mixed for 6 hours. The drug resin complex was washed, dried, and screened through a 60 mesh screen.

The following dissolution was obtained:

| TIME, MINUTES | % PSEUDOEPHEDRINE RELEASED IN 0.1N HCl |
|---|---|
| 15 | 64 |
| 30 | 66 |
| 60 | 67 |
| 90 | 68 |

As is evident from the data the initial release of the drug is very rapid and, therefore, coating the resin drug complex should be beneficial in prolonging dissolution of the drug.

b. Preparation of Polyethylene glycol treated Amberlite XE-69 Pseudoephedrine Resin Complex:

| | |
|---|---|
| Amberlite XE-69 Pseudoephedrine Resin complex | 950 gm |
| Polyethylene Glycol 4000 | 216.1 gm |
| Deionized water | 345 ml |

The resin complex was weighed into a planetary mixer bowl.

The polyethylene glycol was dissolved in the water and the solution was added to the resin complex slowly with mixing. The material was dried in an oven at 45° C. and screened through #40 mesh screen. It was then screened through #60 screen prior to coating.

c. Preparation of coated Amberlite XE-69 pseudoephedrine resin

| | |
|---|---|
| Core: | |
| Polyethylene glycol treated XE-69 Pseudoephedrine Resin complex product from (b) above | 550 g |
| Coating: | |
| Ethylcellulose 50 cps. | 75 g |
| Durkex 500 refined vegetable oil | 30 g |
| Solvent: | |
| Acetone | 140 ml |
| Methylene Chloride, sufficient to make | 1400 ml |

The coating agents were dissolved in the solvents as described in the previous examples and the solution applied on the core material in a fluid bed apparatus. The inlet air temperature ranged from 119°-144° F. The outlet air temperature ranged from 68°-80° F.

The following dissolution data was obtained

| TIME, MINUTES | % PSEUDOEPHEDRINE RELEASED IN 0.1N HCl |
|---|---|
| 15 | 12 |
| 30 | 17 |
| 60 | 23 |
| 90 | 27 |
| 120 | 31 |

It is evident from the above data that coating retards the dissolution of pseudoephedrene from resin drug complex particles. Thus coated/uncoated mixtures of pseudoephedrine resin complex can be made to match any desirable dissolution profile as exemplifed under phenylpropanolamine examples.

EXAMPLE 21

Ephedrine: Ephedrine is also a sympathomimetic agent. It is used in the dose range of 15-60 mg by mouth three or four times a day. It is of value in preventing spasm in asthma. It has a pKa of 9.5 and a biological half life of about 6 hours in man.

Ephedrine is, therefore, a candidate for prolonged release dosage form.

a. Preparation of Amberlite XE-69 Ephedrine Resin Complex:

The Amberlite XE-69 Ephedrine Resin Complex was prepared as described in Example 20.

The following dissolution was obtained:

| TIME, MINUTES | % EPHEDRINE RELEASED ON 0.1N HCl |
|---|---|
| 15 | 63 |
| 30 | 66 |
| 60 | 68 |
| 90 | 69 |

As is evident from the data, the initial release of the drug is very rapid and, therefore, coating the resin drug complex particles should be beneficial in prolonging dissolution of the drug.

b. Preparation of Polyethylene glycol treated Amberlite XE-69 Ephedrine Resin Complex:

| | |
|---|---|
| Amberlite XE-69 Ephedrine Resin Complex | 978.0 gm |
| Polyethylene glycol 4000 | 225.0 gm |
| Deionized water | 359 ml. |

The resin complex was weighed into a planetary mixer bowl. The polyethylene glycol was dissolved in the water and the solution was added to the resin complex slowly with mixing. The material dried in an oven at 45° C. and screened through #40 mesh screen. It was then screened through #60 screen prior to coating.

c. Preparation of coated Amberlite XE-69 Ephedrine resin complex:

| | |
|---|---|
| Polyethylene glycol treated XE-69 Ephedrine Resin Complex product from (b) above | 550 g |
| Coating: | |
| Ethylcellulose 50 cps. | 75 g |
| Durkex 500 refined vegetable oil | 30 g |
| Solvent: | |
| Acetone | 140 ml |
| Methylene Chloride, Sufficient to make | 1400 ml. |

The coating agents were dissolved in the solvents as described in the previous examples and the solution applied on the core material in a fluid bed apparatus. The inlet air temperature ranged from 121°-140° F. The outlet air temperature ranged from 68°-84° F.

The following dissolution data was obtained:

| TIME, MINUTES | % EPHEDRINE RELEASED IN 0.1N HCl |
|---|---|
| 15 | 11 |
| 30 | 16 |
| 60 | 22 |
| 90 | 26 |
| 120 | 29 |

It is evident from the above data that coating retards the dissolution of ephedrine from resin drug complex particles. Thus coated/uncoated mixtures of ephedrine resin complex can be made to match any desirable dissolution profile as exemplified under phenylpropanolamine examples.

EXAMPLE 22

Phentermine (or phenyl-tertiary-butyl-amine) is a sympathomimetic agent. It is used as an anorectic drug. It is rapidly absorbed from the gastrointestinal tract in the free form. Blood levels obtained in humans with the hydrochloride salt in doses of 15 mg. and 30 mg. have produced rapid peak concentrations. Phentermine resin complex, according to U.S. Pat. No. 2,990,332, has been used to delay the release of the drug in the gastrointestinal tract. The following experiments indicate that the release of phentermine may be further prolonged when the phentermine resin complex is subjected to the scope of this invention. These phentermine resin complex particles are 20–60 mesh (250–840 μm).

a. Preparation of Coated Amberlite IR-120 Phentermine Resin complex-lower level-coating

| | |
|---|---|
| Amberlite IR-120-Phentermine Resin Complex (20.93% drug load) | 270 gm. |
| Polyethylene Glycol 4000 | 30 gm. |
| Deionized water | 96 ml. |

The Amberlite IR-120 phentermine resin complex was placed in a suitable mixer. The polyethylene glycol 4000 was dissolved in the specified quantity of deionized water and added gradually to the resin complex in the mixer. To mass was well mixed and dried in a fluid bed drier. The dried material was then screened through a #16 mesh screen. The screened particles were then coated in fluid bed coating apparatus with the following coating solution:

| | |
|---|---|
| Ethylcellulose 50 cps | 10 gm. |
| Durkex 500-refined vegetable oil | 4 gm. |
| Acetone | 40 ml. |
| Methylene Chloride sufficient to make | 400 ml. |

Coating conditions-inlet temperature 94°–101° F. Outlet temperature 76°–86° F. Coating time 49 minutes. Rate of application of the coating solution 8.1 ml/minute. Twenty grams of the coated particles were removed. The phentermine content in the particles was found to be 17.53%. The dissolution results are summarized in the table at the end of the example.

b. Preparation of coated Amberlite IR-120 phentermine resin complex-higher level of coating.

The remaining coated Amberlite IR-120 phentermine resin complex from (a) above (approximately 294 gm.) was further coated with the following solution:

| | |
|---|---|
| Ethylcellulose 50 cps | 5 gm. |
| Durkex 500-refined vegetable oil | 2 gm. |
| Acetone | 20 ml. |
| Methylene Chloride sufficient to make | 200 ml. |

The coating conditions were: inlet temperature 88°–103° F., outlet temperature 78°–87° F.; coating time 65 minutes. The phentermine content in the finished product was found to be 16.14%. The dissolution results are summarized in the following table. Some retardation in the release of phentermine due to coating is evident. The higher level of coating provides more retardation than the lower level of coating.

| | % PHENTERMINE RELEASED IN 0.1N HCl | | |
|---|---|---|---|
| Time Hours | Uncoated Complex | Coated Complex (lower level coating) | Coated Complex (higher level coating) |
| 1.0 | 30 | 28 | 27 |
| 1.5 | 40 | 35 | 32 |
| 2.0 | 44 | 40 | 38 |
| 3.0 | 51 | 45 | 41 |
| 4.0 | 55 | 48 | — |
| 5.0 | 60 | 50 | — |

Thus, coated/uncoated mixtures of phentermine resin complex can be made to match any desirable dissolution profile.

What is claimed is:

1. A pharmaceutical preparation comprising ion exchange resin particles having a pharmacologically active drug absorbed thereon to form drug-resin complex particles, which resin particles have been treated in an amount sufficient to retard their rate of swelling in water with an impregnating agent selected from the group consisting of polyethylene glycol, propylene glycol, mannitol, lactose and methylcellulose, and which treated particles have been subsequently coated with a water-permeable diffusion barrier.

2. A pharmaceutical preparation as in claim 1 wherein the impregnating agent is polyethylene glycol.

3. A pharmaceutical preparation as in claim 2 wherein the coating is comprised of ethyl cellulose.

4. The preparation of claim 3 wherein the drug is phenylpropanolamine.

5. The preparation of claim 3 wherein the drug is dextromethorphan.

6. The preparation of claim 3 wherein the drug is ephedrine.

7. The preparation of claim 3 wherein the drug is pseudoephedrine.

8. The preparation of claim 3 wherein the drug is phentermine.

* * * * *

UNITED STATES PATENT AND TRADEMARK OFFICE
CERTIFICATE OF CORRECTION

PATENT NO. : 4,221,778
DATED : September 9, 1980
INVENTOR(S) : Yegnaswami Raghunathan It is certified that error appears in the above—identified patent and that said Letters Patent is hereby corrected as shown below:

Column 20, line 33 reads:

"tive drug absorbed thereon to form drug-resin complex"

It should read:

-- tive drug adsorbed thereon to form drug-resin complex --

Signed and Sealed this

Eighteenth Day of November 1980

[SEAL]

Attest:

SIDNEY A. DIAMOND

Attesting Officer

Commissioner of Patents and Trademarks